United States Patent
Pigamo et al.

(10) Patent No.: US 8,680,346 B2
(45) Date of Patent: Mar. 25, 2014

(54) PROCESS FOR THE PREPARATION OF TRIFLUORINATED AND TETRAFLUORINATED COMPOUNDS

(75) Inventors: Anne Pigamo, Francheville (FR); Michel Devic, Sainte-Foy-les-Lyon (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 298 days.

(21) Appl. No.: 13/063,079

(22) PCT Filed: Sep. 11, 2009

(86) PCT No.: PCT/IB2009/006803
§ 371 (c)(1),
(2), (4) Date: Mar. 9, 2011

(87) PCT Pub. No.: WO2010/029419
PCT Pub. Date: Mar. 18, 2010

(65) Prior Publication Data
US 2011/0160498 A1    Jun. 30, 2011

(30) Foreign Application Priority Data
Sep. 11, 2008  (FR) .................................... 08 05000

(51) Int. Cl.
*C07C 17/00*    (2006.01)
(52) U.S. Cl.
USPC ............................ 570/196; 570/155; 570/164
(58) Field of Classification Search
USPC ........................................ 570/155, 164, 196
See application file for complete search history.

(56) References Cited

U.S. PATENT DOCUMENTS

2010/0072415 A1*  3/2010  Rao et al. ......................... 252/67
2010/0145111 A1*  6/2010  Sharratt et al. ................ 570/156

FOREIGN PATENT DOCUMENTS

WO        2008075017 A2    6/2008

OTHER PUBLICATIONS

Rao et al., WO 2008054781 Chemical abstract, 2008.*
International Search Report dated Mar. 2, 2010, issued in corresponding PCT/IB2009/006803.
Haszeldine, R. N., "Reactions of Fluorocarbon Radicals Part V.*Alternative Synthesis for Trifluoromethylacetylene (3:3:3-Trifluoropropyne), and the Influence of Polyfluoro-groups on Adjacent Hydrogen and Halogen Atoms," Journal of the American Chemical Society, 1951, pp. 2495-2504, XP002503499.
Buchner, M. et al, "Reactions of Gaseous, Halogenated Propene Radical Cations with Ammonia: A Study of the Mechanism by Fourier Transform Ion Cyclotron Resonance," Chemistry—A European Journal, vol. 4, 1998, pp. 1799-1809, XP002517111.
World IP Organization. "Translation-Written Opinion of the International Searching Authority" PCT/IB2009/006803, Applicant: Arkema France, Authorized Officer: Cecile Chatel, Apr. 12, 2011.

* cited by examiner

*Primary Examiner* — Jafar Parsa
(74) *Attorney, Agent, or Firm* — Millen, White, Zelano & Branigan, P.C.

(57) ABSTRACT

The subject of the invention is a process for the preparation of 2,3-dichloro-1,1,1-trifluoropropane by chlorination of 3,3,3-trifluoropropene at a pressure greater than 2 bar. Application in the synthesis of 1234yf.

12 Claims, No Drawings

US 8,680,346 B2

PROCESS FOR THE PREPARATION OF TRIFLUORINATED AND TETRAFLUORINATED COMPOUNDS

FIELD OF THE INVENTION

The invention concerns a process for the preparation of fluorinated compounds, namely the 2,3-dichloro-1,1,1-trifluoropropane compound (243db), from which the fluorinated compound 2,3,3,3-tetrafluoro-1-propene (HFO 1234yf) can be produced.

TECHNOLOGICAL BACKGROUND

The hydrofluorocarbons (HFC) and in particular the hydrofluoroolefins such as 2,3,3,3-tetrafluoro-1-propene (HFO 1234yf) are compounds known for their properties as refrigerants and heat-transfer fluids, extinguishers, propellants, foaming agents, swelling agents, gaseous dielectrics, polymerization or monomer media, support fluids, abrasive agents, drying agents and fluids for energy production units. Unlike CFCs and HCFCs, which are potentially dangerous for the ozone layer, HFOs do not contain chlorine and therefore do not pose a problem for the ozone layer.

Several processes for producing 1234yf are known.

WO2007/079431 describes the preparation of 1234yf by a process comprising the fluorination steps of 1233xf to 1,1,1,2-tetrafluoro-2-chloropropane (HFC244bb), followed by a dehydrochlorination step. The product 1233xf is prepared by trifluorination of the corresponding chlorinated precursor ($CCl_2=CClCH_2Cl$).

WP2008/054781 describes a preparation of 1234yf by reaction of 2,3-dichloro-1,1,1-trifluoropropane (243db) in the presence of HF on a catalyst, in particular the catalyst consisting in Cr/Co 98/2. The products of the reaction comprise 1234yf and 2-chloro-3,3,3-trifluoro-1-propene (1233xf), the latter product forming the major proportion; the other products 1-chloro-3,3,3-trifluoro-1-propene (1233zd) as well as 245cb and 1234ze are also formed. A higher temperature promotes the production of the isomer 1233zd. The starting product 2,3-dichloro-1, 1,1-trifluoropropane (243db) is indicated, without further details, as being obtained by chlorination of the trifluoro-1-propene (TFP).

WO2008/040969 and WO2008/075017 describe a substantially similar preparation. It is indicated that the reaction proceeds by dehydrochlorination of 243db to 1233 (xf as well as zd), followed by a reaction involving the formation of 1,1,1,2-tetrafluoro-2-chloropropane and the subsequent formation by dehydrochlorination of the 2,3,3,3-tetrafluoro-1-propene sought. The HF/organics ratio is varied and it is indicated that the dehydrochlorination reaction to 1233 (xf and zd) is promoted by low HF/organics ratios while the reaction of preparation of the final compound sought is promoted by high HF/organics ratios.

The starting product 2,3-dichloro-1,1,1-trifluoro-propane (243db) is indicated as being obtained by chlorination, without further details. of trifluoropropene or trifluoromethylpropene, In these documents, no detail is given with respct of the preparation of the starting product, 243db. Although the chlorination reactions, in particular olefin chlorination, are known, there is no accurate description in the state of the art of a chlorination step of TFP to 243db.

WO 2005108334 describes the addition of a compound $X_1X_2$ to trifluoropropene, with $X_1$ and $X_2$ which can be independently chlorine. The addition of $Cl_2$ to TFP is also indicated, as the first step before a fluorination reaction. However, the only examples relating to TFP are carried out with bromine and iodine, and furthermore in the presence of HF; in this document the 2,3-dibrominated or 2,3-diiodinated compound is neither isolated nor prepared.

The effective chlorination reaction of TFP to 243db is therefore not described in full in the technical literature.

There is a need for a process for the preparation of 1234yf from a starting product which is easily accessible, and which results in the obtaining of the sought product showing a high selectivity and advantageously a high yield and/or conversion.

There is also a need for a process for the preparation of 243db, a useful precursor in the preparation of 1234yf from a starting product which is easily accessible, and which results in the sought product showing a high selectivity and advantageously a high yield and/or conversion.

SUMMARY OF THE INVENTION

The invention therefore provides a process for the preparation of 2,3-dichloro-1,1,1-trifluoropropane by chlorinetion of 3,3,3-trifluoropropene at a pressure greater than 2 bars.

According to an embodiment, the pressure is comprised between 4 and 50 bars, preferably between 5 and 20 bars, advantageously under autogenous pressure.

According to an embodiment, this process is carried out in the liquid phase.

According to an embodiment, this process is carried out in the absence of added catalyst.

A subject of the invention is also a process for the preparation of 2,3,3,3-tetrafluoro-1-propene comprising the following steps:
  (i) chlorination of 3,3,3-trifluoropropene to 2,3-dichloro-1,1,1-trifiuoropropane by the process described above for the preparation of 243db;
  (ii) dehydrochlorination of the 2,3-dichloro-1,1,1-tri-fluoropropane obtained in the previous step to 2-chloro-3,3,3-trifluoro-1-propene; and
  (iii) fluorination of the 2-chloro-3,3,3-trifiuoro-1-propene obtained in the previous step to 2,3,3,3-tetrafluoro-1-propene.

In this process, according to an embodiment, step (iii) consists in a direct catalytic fluorination.

According to a further embodiment, in this process, step (iii) comprises a first sub-step (iiia) of hydrofluorination to 1,1,1,2-tetrafluoro-2-chloropropane and a second sub-step (iiib) of dehydrochlorination to 2,3,3,3-tetrafluoro-1-propene.

According to another embodiment, in this process, steps (ii) and (iii) are operated in the gaseous phase.

According to another further embodiment, in this process, step (ii) is operated in the presence of hydrogen.

According to an embodiment, in this process, the dehydrochlorination reaction(s) is(are) operated in the presence of HF, the HF/starting product ratio being comprised between 1/1 and 5/1.

DETAILED DESCRIPTION OF EMBODIMENTS

The invention uses a step of chlorination of 3,3,3-trifluoropropene (1243zf) to 2,3-dichloro-1,1,1-trifluoro-propane (243db).

According to the invention, this step is in particular carried out under a pressure greater than 2 bars. Advantageously, the pressure is comprised between 4 and 50 bars, in particular between 5 and 20 bars. It is possible to work at autogenous pressure (approximately 6 bars), in the presence or in the absence of ballast gas resulting in an increased pressure in the medium. This inert gas can be helium in particular. Advantageously, there is no ballast gas in the system.

The reaction is carried out either in the gaseous phase or in the liquid phase, preferably in the liquid phase. Both reagents or only one of the two can be gaseous. In particular, the TFP can be in gaseous or liquid form, advantageously in liquid form. Under autogenous pressure, (approximately 6 bars), the TFP is in the liquid form. Without wishing to be bound by any theory, the Applicant considers that the (liquid) TFP thus acts as a solvent.

The reaction product is liquid (in particular at ambient temperature).

The $Cl_2$/TFP molar ratio is comprised between 0.1/1 and 10/1, preferably 0.2/1 to 5/1, advantageously between 0.5/1 and 1/1. The benefit of carrying out the reaction in stoechiometric quantity is avoiding the loss of excess of trifluoropropene. However, taking account of the exothermic nature of the reaction, it can be beneficial to carry out the reaction with an excess of TFP in the reactor, for example with a $Cl_2$/TFP molar ratio of 0.5. The trifluoropropene will then be recycled.

The duration of the chlorination reaction is variable and can be comprised between 0.1 and 50 hours, preferably between 0.3 and 5 hours, advantageously between 0.5 and 3 hours.

The reaction temperature can be very variable. For example, it can be comprised between 0° C., advantageously 20° C. (approximately ambient temperature) and 200° C., preferably between 20° C. and 150° C., advantageously between 40 and 100° C.

The reaction is an exothermic reaction (the heat of reaction is estimated at $\Delta H=-200$ kJ/mol). The reaction temperature can be controlled or not. If it is desired to control the reaction temperature, a reactor having a system of regulation can be used (e. g. double-jacketed) and the setting temperature can be adjusted. The latter can be varied for example between 20 and 100° C., advantageously between 30 and 80° C. The exothermic nature of the reaction leads in general to a rapid increase in temperature at the starting of the reaction, for example up to a temperature of 100° C., then temperature drops to the setting temperature of the reactor. The use of a double-jacketed reactor or equivalent system is standard and well known to any person skilled in the art.

The reaction can be carried out in the presence of a catalyst, for example an iron-based catalyst (in the form of metal or $FeCl_3$). Advantageously the reaction is carried out in the absence of added catalyst, which simplifies the reaction.

The reaction product can be subjected to separation steps such as distillation, washing, etc., according to standard methods known to any person skilled in the art.

According to an embodiment, the crude product is subjected to a filtration (after maintaining the crude reaction product to rest). The filtration makes it possible to recover any solid deposit present in the reaction medium. This filtration is carried out over a membrane, for example of the Millipore® type, with a variable size, for example between 0.01 and 5 µm; preferably between 0.05 and 1 µm, advantageously between 0.1 and 0.5 µm. This resting period of the crude reaction product is comprised between 1 and 30 days, preferably between 2 and 10 days. The filtration can be carried out under vacuum. Thus the 243db product is obtained simply, whilst eliminating the major part of the TiP (the filtration under vacuum makes it possible, for example at ambient conditions, to draw off the TiP, the boiling point of which is below 0° C. under normal pressure).

The chlorination reaction (preferably in the liquid phase) under pressure can therefore be carried out under extremely simple conditions (in particular without the use of a catalyst, and by operating under autogenous pressure) and is very efficient. The selectivity of the 243db product is in general greater than 90%, preferably greater than 95%, advantageously greater than 98%, or even greater than 99%. The conversion of chlorine to the 243db product is in general greater than 80%, advantageously greater than 90%, or even greater than 95%.

According to another aspect, the invention is a process for the preparation of 1234yf in three steps, the first of which is the TiP chlorination step described above.

The reactions can be carried out in series, carried out in line or not, carried out in liquid or gaseous phase (the first step being carried out very advantageously in the liquid phase), the reaction products being sent to the following step, optionally after having undergone for example, if necessary, a separation treatment.

The second step of the process is a dehydrochlorination reaction of the 2,3-dichloro-1,1,1-trifluoropropane (243db) product obtained at the previous step to 2-chloro-3,3,3-trifluoro-1-propene (1233xf).

The dehydrochlorination reactions are carried out according to classical methods by any person skilled in the art.

The dehydrochlorination reaction is preferably carried out with a dehydrochlorination catalyst. This catalyst is for example a metal-based catalyst, in particular a transition metal or an oxide or halide or oxyhalide derivative of such metal. The catalysts are for example $FeCl_3$, chromium oxyfluoride, Ni (including Ni mesh), $NiCl_2$, $CrF_3$, and their mixtures, for example Ni—Cr/$AlF_3$. Other possible catalysts are catalysts supported on carbon, catalysts based on antimony, catalysts based on aluminium (such as $AlF_3$ and $Al_2O_3$ and aluminium oxyfluoride and fluorinated alumina), on palladium, platinum, rhodium and ruthenium. Reference may be made to the list given U.S. Pat. No. 5,396,000, column 1, line 50 to column 2, line 2 or to the list given in WO 2007/056194, page 16, lines 13-23. It is also possible to use the catalysts described in WO 2008/040969, and in particular Zn on chromium oxide, treated with HF.

This dehydrochlorination step is carried out at a temperature comprised for example between 220 and 400° C., preferably between 250 and 380° C.

The contact time (ratio between the volume of catalyst and the total flow of the feed stock) is in general comprised between 0.1 and 100 seconds, preferably between 1 and 50 seconds.

This reaction can be carried out in the gaseous phase (optionally in the presence of an inert diluting gas) or in the liquid phase. The gaseous phase will be preferred.

When the dehydrochlorination reaction is carried out in the liquid phase, the dehydrochlorination agent is in particular KOH. This. KOH is in particular available in the form of an aqueous solution having a KOH content from to 50% by weight. The temperature is for example comprised between −10 and 10° C. Heat can be removed by a suitable device. The reaction time can be comprised between 1 and 50 hours.

The dehydrochlorination reaction (in particular in the gaseous phase) can be carried out in the absence or in the presence of HF. If HF is used, it can be used in a molar ratio less than 5/1 with respect to the organic load (243db), or also in a ratio comprised between 5/1 and 15/1. Higher ratios, for example from 5/1 to 50/1, can be envisaged. Low ratios, for example comprised between 1/1 and 5/1, will be preferred.

The presence of HF (in variable ratios) during the dehydrochlorination reaction, in particular when the temperature is comprised between 280 and 380° C. can lead in the direct production, in the sought final product, of 1234yf product, as well as in the 1233xf product.

It is also possible that 1,1,1,2,2-pentafluoropentane is produced; this compound can easily undergo a dehydrofluorination reaction to produce the 1234yf final product sought; reference may be made to Example 2 of WO 2008/040969 regarding this point.

Catalyst regeneration steps can also be provided, in a known manner.

The pressure in the different reactions, in the gaseous phase, can be atmospheric pressure, or below or above this atmospheric pressure.

The dehydrochlorination reaction can lead to two compounds, consisting in position isomers, 2-chloro-3,3,3-trifluoro-1-propene (1233xf) and 1-chloro-3,3,3-trifluoro-1-propene (1233zd). If the isomer that is not sought is present, it can be separated at this step from the reaction mixture. It can also remain in the reaction medium, and the subsequent reaction products can optionally be separated later, if necessary.

Preferably, the dehydrochlorination reaction preferentially produces the compound 1233xf. Preferably, the selectivity is greater than 80%, advantageously greater than 90% and more advantageously greater than 95%. According to the embodiment in which 1234yf is produced concomitantly, the selectivity is expressed by taking account of the two compounds 1233xf and 1234yf.

It is also possible to operate in the presence of hydrogen in order to improve the selectivity of product 1233xf.

The conversion is also preferably very high, greater than 50%, advantageously greater than 70%, preferably greater than 90%, or even greater than 95%.

In general, hydrogen can be injected with the starting feed stock, for example continuously. The molar ratio $H_2$/starting feed stock can vary widely, in particular between 0.3 and 30, in particular between 0.5 and 20, advantageously between 1 and 10.

Implementation of the dehydrochlorination reactions in the presence of hydrogen therefore allows a high selectivity. The presence of hydrogen also makes it possible to reduce the production of heavy elements during the reaction.

An example of a dehydrochlorination reaction of 243db to 1233xf (and 1234yf) is given in the documents cited above, for example WO2008/054781, WO2008/040969 and WO2008/075017. Reference may be made in particular to the document WO 2008/040969, and in particular pages 16 and 17, route A, and Example 1.

The third step of the process for the preparation of 1234yf is a fluorination reaction of 2-chloro-3,3,3-trifluoro-1-propene (1233xf) obtained in the previous step to 2,3,3,3-tetrafluoro-1-propene, the sought product.

This third step can comprise direct fluorination, in the gaseous phase, in the presence of HF and on a catalyst,. Fluorination catalysts which can be used are for example chromium oxyfluoride, aluminium fluoride and oxyfluoride, a supported catalyst containing a metal such as Cr, Zn, Ti, V, Zr, Mo, Ge, Sn, Pb. The temperatures, pressures and contact time are easily determined by any person skilled in the art.

Such a process is described with reference to the compound 1233zd which allows to obtain compound 1234ze, in EP-A-1067106, (in particular Example 1), to which reference is made. The application of the process to the starting product 1233xf will result in the formation of the product 1234yf. The concomitant formation of the hydrofluorination product is possible, although not sought. The saturated reaction product can then be dehydrohalogenated, under conditions similar to those of the second step of the present process, in order to result in the sought product.

This third step can also comprise two sub-steps, a first sub-step of formation of the product 1,1,1,2-tetrafluoro-2-chloropropane (244bb), then a second sub-step of dehydrochlorination of this product to the sought 1234yf.

The first sub-step comprises the hydrofluorination of the 1233xf, which can be carried out under known conditions. For example, the reaction can be carried out in liquid or gaseous phase, on a catalyst which can be a Lewis acid, or a metal halide, such as for example $SbCl_5$, $SbCl_3$, $SbF_5$, $SnCl_4$, $TiCl_4$, $FeCl_3$, etc. The temperature can be comprised between 50° C. and 400° C., for example from 150° C. to 300° C. The contact time is determined as a function of the conversion and selectivity sought. The first sub-step is in particular described in the document WO 2007/079431, page 8, line 17 to page 10, line 16 and Examples 5A, 5B and 6, to which it refers. Reference may therefore also be made to the document WO 2008/040969, pages 16 & 17. In this reaction, the HF/1233xf ratio is preferably greater than 5/1, and in general comprised between 5/1 and 50/1, or also between 15/1 and 30/1, in order to promote the fluorination reaction.

The second sub-step is a dehydrochlorination step, which is carried out under the conditions described above for the dehydrochlorination reaction of the second step of the process for the preparation of 1234yf. For this second sub-step reference may be made to the document WO 2007/079431, page 10, line 18 to page 12, line 14 and Example 6, to which it refers. Reference may also be made to the document WO 2008/040969, pages 16 & 17.

When the second step of the process leads to the formation of compound 1233zd, this compound can optionally be subjected to the conditions of this third step when it is carried out with using the two sub-steps. In such a case, the first sub-step results in the compound $CF_3$—CHF—$CH_2Cl$ (244eb), which is in turn dehydrochlorinated to the sought product. The latter reaction is also covered by the generic description given in document WO 2007/056194 already cited above.

The reactions are carried out in one or more reactors dedicated to reactions involving the presence of halogens. Such reactors are known to any person skilled in the art, and can comprise internal coatings based for example on Hastelloy®, Inconel®, Monel® or fluoropolymers. The reactor can also comprise heat exchange means, if necessary.

The supply of reagents can in general be carried out continuously, or can be in steps if appropriate. The point(s) for any separation and/or recycling are variable, at the start of the process or at intermediate levels.

EXAMPLES

The following examples illustrate the invention without limiting it (the pressures are in bars).

Example 1

The apparatus used is constituted by a double-jacketed autoclave with a capacity of 1 liter, made of 316L stainless steel, and comprising stirring means. The latter is equipped with a pressure and temperature gauge. Inlets at the top of the autoclave allow the introduction of the reagents and degassing. A tightness test is carried out after the solid catalyst having been introduced, namely a metallic test coupon of 46 g of iron previously scoured in a solution of hydrochloric acid. 1.098 mol (78 g) chlorine is introduced into the reactor previously placed under vacuum and cooled in liquid nitrogen. 1.098 mol (105.5 g) trifluoropropene are then added. The autogenous pressure is approximately of 6 bars. The reactor is pressurized to 10 bars absolute using helium. The reaction medium is left under stirring for 4 hours. The reactor is then slowly depressurized. In this way 163.4 g of a slightly yellow cloudy liquid is recovered at the bottom of the reactor. The nature of this liquid is analyzed using a gas chromatograph equipped with a Carbopack® Bl % SP1000 column. The liquid recovered is constituted mainly by 243db (98.0 mol %) and residual TFP (1.4 mol %) (dissolved in the 243db). A very small quantity of impurities was nevertheless identified, originating from a radical reaction mechanism: $CF_3$—$CCl=CH_2$, $CF_3$—$CH_2$—$CH_2Cl$, $CF_3$—$CHCl$—$CH_2Cl$. The gaseous phase was also analyzed and contains 22% TFP and 77.4% 243db. Taking account of the reactor headspace volume (800 ml), the pressure of 6 bars and the temperature on degassing, 0.038 mol TFP is calculated in the gaseous phase and 0.134 mol of 243db. The conversion of the TFP is therefore 95.3% and the selectivity for 243db greater than 99%.

Filtration over a Millipore® 0.22 µm membrane makes it possible to obtain a transparent liquid and at the same time to eliminate a portion of the residual trifluoropropene. The resulting solution of 243 db has a purity of 99.05% with 0.7% trifluoropropene.

The invention claimed is:

1. A process for the preparation of 2,3-dichloro-1,1,1-trifluoropropane, comprising chlorinating by chlorination of 3,3,3-trifluoro-propene at a pressure greater than 2 bars.

2. The process according to claim 1, wherein the pressure is 4 to 50 bars.

3. The process according to claim 1, carried out in liquid phase.

4. The process according to claim 1, carried out in absence of added catalyst.

5. A process for the preparation of 2,3,3,3-tetrafluoro-1-propene, comprising:
  (i) chlorinating 3,3,3-trifluoropropene to 2,3-di-chloro-1,1,1-trifluoropropane by the process of claim 1;
  (ii) dehydrochlorinating the 2,3-dichloro-1,1,1-tri-fluoropropane obtained to 2-chloro-3,3,3-trifluoro-1-propene;
  (iii) fluorinating the 2-chloro-3,3,3-trifluoro-1-propene obtained to 2,3,3,3-tetrafluoro-1-propene.

6. The process according to claim 5, in which (iii) is a direct catalytic fluorination.

7. The process according to claim 5, in which (iii) comprises (iiia) hydrofluorinating to 1,1,1,2-tetrafluoro-2-chloropropane and (iiib) hydrofluorinating to 2,3,3,3-tetrafluoro-1-propene.

8. The process according to claim 5, in which (ii) and (iii) are carried out in gaseous phase.

9. The process according to claim 5, in which (ii) is carried out in presence of hydrogen.

10. The process according to claim 5, in which dehydrochlorination is carried out in the presence of HF in an HF/starting product ratio of 1/1 to 5/1.

11. The process according to claim 2, wherein the pressure is 5 to 20 bars.

12. The process according to claim 2, wherein the pressure is autogeneous.

* * * * *